US011151160B2

(12) United States Patent
Motivala et al.

(10) Patent No.: US 11,151,160 B2
(45) Date of Patent: *Oct. 19, 2021

(54) CLONING CATALOG OBJECTS

(71) Applicant: Snowflake Inc., San Mateo, CA (US)

(72) Inventors: Ashish Motivala, Foster City, CA (US); Benoit Dageville, Foster City, CA (US)

(73) Assignee: Snowflake Inc., Bozeman, MT (US)

(*) Notice: Subject to any disclaimer, the term of this patent is extended or adjusted under 35 U.S.C. 154(b) by 0 days.

This patent is subject to a terminal disclaimer.

(21) Appl. No.: 16/814,443

(22) Filed: Mar. 10, 2020

(65) Prior Publication Data

US 2020/0210448 A1 Jul. 2, 2020

Related U.S. Application Data

(63) Continuation of application No. 16/741,693, filed on Jan. 13, 2020, now Pat. No. 10,866,966, which is a
(Continued)

(51) Int. Cl.
*G06F 16/00* (2019.01)
*G06F 16/27* (2019.01)
(Continued)

(52) U.S. Cl.
CPC .......... *G06F 16/27* (2019.01); *G06F 9/4881* (2013.01); *G06F 9/5016* (2013.01);
(Continued)

(58) Field of Classification Search
CPC .... G06F 16/27; G06F 9/5083; G06F 16/2365; G06F 16/1827; G06F 16/24532;
(Continued)

(56) References Cited

U.S. PATENT DOCUMENTS 5,787,466 A 7/1998 Berliner
6,209,128 B1 * 3/2001 Gerard ...................... G06F 8/70
707/999.202
(Continued)

FOREIGN PATENT DOCUMENTS

CN 102496060 6/2012
CN 203261358 10/2013
(Continued)

OTHER PUBLICATIONS

Stokley et al., "Storage provisioning and allocation in a large cloud environment", Sep. 2012, 2 pages.
(Continued)

*Primary Examiner* — Alexander Khong
(74) *Attorney, Agent, or Firm* — Womble Bond Dickinson (US) LLP

(57) ABSTRACT

Example systems and methods for cloning catalog objects are described. In one implementation, a method includes creating a copy of a catalog object without copying a data associated with the catalog object by only coping metadata associated with the object. The method further includes modifying, by one or more processors, the data associated with the catalog object independently of the copy of the catalog object.

24 Claims, 11 Drawing Sheets

Related U.S. Application Data continuation of application No. 15/171,859, filed on Jun. 2, 2016, now Pat. No. 10,534,793, which is a continuation-in-part of application No. 14/518,884, filed on Oct. 20, 2014, now Pat. No. 10,366,102.

(60) Provisional application No. 61/941,986, filed on Feb. 19, 2014.

(51) Int. Cl.

| | | |
|---|---|---|
| G06F 9/50 | (2006.01) | |
| G06F 16/14 | (2019.01) | |
| G06F 16/21 | (2019.01) | |
| G06F 16/22 | (2019.01) | |
| G06F 16/951 | (2019.01) | |
| G06F 16/182 | (2019.01) | |
| G06F 16/23 | (2019.01) | |
| G06F 16/2455 | (2019.01) | |
| G06F 16/2458 | (2019.01) | |
| G06F 16/9535 | (2019.01) | |
| G06F 16/2453 | (2019.01) | |
| G06F 9/48 | (2006.01) | |
| H04L 29/08 | (2006.01) | |

(52) U.S. Cl.
CPC .......... *G06F 9/5044* (2013.01); *G06F 9/5083* (2013.01); *G06F 9/5088* (2013.01); *G06F 16/148* (2019.01); *G06F 16/1827* (2019.01); *G06F 16/211* (2019.01); *G06F 16/221* (2019.01); *G06F 16/2365* (2019.01); *G06F 16/2456* (2019.01); *G06F 16/2471* (2019.01); *G06F 16/24532* (2019.01); *G06F 16/24545* (2019.01); *G06F 16/24552* (2019.01); *G06F 16/951* (2019.01); *G06F 16/9535* (2019.01); *H04L 67/1095* (2013.01); *H04L 67/1097* (2013.01); *H04L 67/2842* (2013.01)

(58) Field of Classification Search
CPC ............. G06F 9/5088; G06F 16/24545; G06F 9/4881; G06F 16/221; G06F 16/951; G06F 9/5044; G06F 16/2471; G06F 16/148; G06F 16/211; G06F 9/5016; G06F 16/2456; G06F 16/9535; G06F 16/24552; H04L 67/1095; H04L 67/1097; H04L 67/2842

See application file for complete search history.

(56) References Cited

U.S. PATENT DOCUMENTS

| | | |
|---|---|---|
| 6,490,590 B1 | 12/2002 | Fink |
| 6,505,227 B1 | 1/2003 | Mirchandaney |
| 6,757,689 B2 | 6/2004 | Battas |
| 7,280,998 B1 | 10/2007 | Aboujaoude |
| 7,823,009 B1 | 10/2010 | Tormasov |
| 8,341,363 B2 | 12/2012 | Chou |
| 8,381,015 B2 | 2/2013 | Kaminski |
| 8,428,087 B1 | 4/2013 | Vincent |
| 8,516,159 B2 | 8/2013 | Ananthanarayanan |
| 8,516,355 B2 | 8/2013 | Gale |
| 8,560,887 B2 | 10/2013 | Behrendt |
| 8,640,137 B1 | 1/2014 | Bostic et al. |
| 8,706,914 B2 | 4/2014 | Duchesneau |
| 8,725,875 B2 | 5/2014 | Supalov |
| 9,152,642 B2 | 10/2015 | Harrison et al. |
| 9,171,042 B1 | 10/2015 | Welton |
| 9,210,100 B2 | 12/2015 | Van Der Linden et al. |
| 9,253,017 B2 | 2/2016 | Adlung et al. |
| 9,335,989 B2 | 5/2016 | Apte et al. |
| 9,417,897 B1 | 8/2016 | Klompje et al. |
| 9,489,423 B1 * | 11/2016 | Muthiah ........... G06F 16/24542 |
| 10,353,878 B1 * | 7/2019 | Mohen .................... G06F 16/22 |
| 2002/0120630 A1 | 8/2002 | Christianson et al. |
| 2003/0158884 A1 | 8/2003 | Alford, Jr. |
| 2004/0098447 A1 | 5/2004 | Verbeke |
| 2004/0167904 A1 | 8/2004 | Wen et al. |
| 2005/0210049 A1 | 9/2005 | Foster |
| 2006/0059173 A1 | 3/2006 | Hirsch et al. |
| 2006/0074872 A1 | 4/2006 | Gordon |
| 2006/0136761 A1 | 6/2006 | Fraiser |
| 2007/0033247 A1 | 2/2007 | Martin |
| 2007/0198656 A1 | 8/2007 | Mazzafer et al. |
| 2007/0276861 A1 | 11/2007 | Pryce et al. |
| 2007/0294692 A1 | 12/2007 | Zhao |
| 2008/0027788 A1 | 1/2008 | Lawrence et al. |
| 2008/0027920 A1 | 1/2008 | Schipunov et al. |
| 2008/0027965 A1 | 1/2008 | Garret et al. |
| 2008/0082644 A1 | 4/2008 | Isard |
| 2009/0182836 A1 | 7/2009 | Aviles et al. |
| 2009/0254516 A1 | 10/2009 | Meiyyappan et al. |
| 2009/0254532 A1 | 10/2009 | Yang et al. |
| 2009/0300043 A1 | 12/2009 | Maclennan |
| 2010/0005054 A1 | 1/2010 | Smith et al. |
| 2010/0031267 A1 | 2/2010 | Maessen et al. |
| 2010/0100888 A1 | 4/2010 | Tene et al. |
| 2010/0107170 A1 | 4/2010 | Stehley |
| 2010/0145929 A1 | 6/2010 | Berger |
| 2010/0179940 A1 | 7/2010 | Gilder et al. |
| 2010/0199042 A1 | 8/2010 | Bates |
| 2011/0145307 A1 | 6/2011 | Ananthanarayanan et al. |
| 2011/0161488 A1 | 6/2011 | Anderson et al. |
| 2011/0225167 A1 | 9/2011 | Bhattacharjee et al. |
| 2011/0302151 A1 | 12/2011 | Abadi et al. |
| 2012/0005307 A1 | 1/2012 | Das et al. |
| 2012/0101860 A1 | 4/2012 | Ezzat |
| 2012/0109888 A1 | 5/2012 | Zhang et al. |
| 2012/0110570 A1 | 5/2012 | Jacobson |
| 2012/0166771 A1 | 6/2012 | Ringseth |
| 2012/0173824 A1 | 7/2012 | Iyigun et al. |
| 2012/0204187 A1 | 8/2012 | Breiter et al. |
| 2012/0233315 A1 | 9/2012 | Hoffman |
| 2012/0260050 A1 | 10/2012 | Kaliannan |
| 2012/0265881 A1 | 10/2012 | Chen |
| 2012/0296883 A1 | 11/2012 | Ganesh et al. |
| 2012/0311065 A1 | 12/2012 | Ananthanarayanan et al. |
| 2012/0323971 A1 | 12/2012 | Pasupuleti |
| 2013/0007753 A1 | 1/2013 | Jain |
| 2013/0110778 A1 | 5/2013 | Taylor et al. |
| 2013/0110961 A1 | 5/2013 | Jadhav |
| 2013/0124545 A1 | 5/2013 | Holmberg et al. |
| 2013/0132967 A1 | 5/2013 | Soundararajan |
| 2013/0145375 A1 | 6/2013 | Kang |
| 2013/0151884 A1 | 6/2013 | Hsu |
| 2013/0174146 A1 | 7/2013 | Dasgupta |
| 2013/0198459 A1 | 8/2013 | Joshi |
| 2013/0205028 A1 | 8/2013 | Crockett et al. |
| 2013/0205092 A1 | 8/2013 | Roy et al. |
| 2013/0218837 A1 | 8/2013 | Bhatnagar |
| 2013/0177239 A1 | 9/2013 | Shinohara et al. |
| 2013/0282795 A1 | 10/2013 | Tsao |
| 2013/0332614 A1 | 12/2013 | Brunk |
| 2014/0013059 A1 | 1/2014 | Joshi |
| 2014/0025638 A1 | 1/2014 | Hu |
| 2014/0059226 A1 | 2/2014 | Messerli |
| 2014/0095646 A1 | 4/2014 | Chan |
| 2014/0109095 A1 | 4/2014 | Farkash |
| 2014/0115091 A1 | 4/2014 | Lee |
| 2014/0136473 A1 | 5/2014 | Faerber |
| 2014/0149461 A1 | 5/2014 | Wijayaratne |
| 2014/0173594 A1 | 6/2014 | Ng et al. |
| 2014/0195558 A1 | 7/2014 | Murthy et al. |
| 2015/0106611 A1 | 4/2015 | Cao et al. |
| 2015/0121371 A1 | 4/2015 | Gummaraju |
| 2015/0234895 A1 | 8/2015 | Erdogan |

(56) References Cited

U.S. PATENT DOCUMENTS

2015/0370641 A1* 12/2015 Susairaj ............... G06F 3/0619
                                                    707/645
2016/0188628 A1    6/2016 Hartman et al.

FOREIGN PATENT DOCUMENTS

| JP | 2005056077 | 3/2005 |
| WO | 2006026659 | 3/2006 |
| WO | 2013006157 | 1/2013 |
| WO | 2013072232 | 5/2013 |
| WO | 2013084078 | 6/2013 |

OTHER PUBLICATIONS

Gupta et al., "MIRAGE: Storage provisioning in large data centers using balanced component utilizations", Jan. 2008, 2 pages.
Casalicchio et al., "Autonomic resource provisioning in cloud systems with availability goals", Aug. 2013, 10 pages.
Aiia Abouzeid et al.: "HadoopDB", Proceedings of the VLDB Endowment; [ACM Digital Library], Assoc, of Computing Machinery, New York, NY, vol. 2, No. 1, Aug. 1, 2009, pp. 922-933.

* cited by examiner

CLONING CATALOG OBJECTS

CROSS REFERENCE TO RELATED APPLICATIONS

This application is a continuation of U.S. patent application Ser. No. 16/741,693, entitled "Cloning Catalog Objects," filed on Jan. 13, 2020, which is a continuation of U.S. patent application Ser. No. 15/171,859, entitled "Cloning Catalog Objects," filed on Jun. 2, 2016, now issued as U.S. Pat. No. 10,534,793, issued on Jan. 14, 2020, which is a continuation-in-part of U.S. patent application Ser. No. 14/518,884, entitled "Resource management systems and methods," filed on Oct. 20, 2014, now issued as U.S. Pat. No. 10,366,102, issued on Jul. 30, 2019, the disclosure of which is incorporated herein by reference in its entirety. That application claims the benefit of U.S. Provisional Application Ser. No. 61/941,986, entitled "Apparatus and method for enterprise data warehouse data processing on cloud infrastructure," filed Feb. 19, 2014, the disclosure of which is also incorporated herein by reference in its entirety.

TECHNICAL FIELD

The present disclosure relates to systems and methods that support data storage and retrieval.

BACKGROUND

Many existing data storage and retrieval systems are available today. For example, in a shared-disk system, all data is stored on a shared storage device that is accessible from all of the processing nodes in a data cluster. In this type of system, all data changes are written to the shared storage device to ensure that all processing nodes in the data cluster access a consistent version of the data. As the number of processing nodes increases in a shared-disk system, the shared storage device (and the communication links between the processing nodes and the shared storage device) becomes a bottleneck that slows data read and data write operations. This bottleneck is further aggravated with the addition of more processing nodes. Thus, existing shared-disk systems have limited scalability due to this bottleneck problem.

Another existing data storage and retrieval system is referred to as a "shared-nothing architecture." In this architecture, data is distributed across multiple processing nodes such that each node stores a subset of the data in the entire database. When a new processing node is added or removed, the shared-nothing architecture must rearrange data across the multiple processing nodes. This rearrangement of data can be time-consuming and disruptive to data read and write operations executed during the data rearrangement. And, the affinity of data to a particular node can create "hot spots" on the data cluster for popular data. Further, since each processing node performs also the storage function, this architecture requires at least one processing node to store data. Thus, the shared-nothing architecture fails to store data if all processing nodes are removed. Additionally, management of data in a shared-nothing architecture is complex due to the distribution of data across many different processing nodes.

The systems and methods described herein provide an improved approach to data storage and data retrieval that alleviates the above-identified limitations of existing systems.

BRIEF DESCRIPTION OF THE DRAWINGS

Non-limiting and non-exhaustive embodiments of the present disclosure are described with reference to the following figures, wherein like reference numerals refer to like parts throughout the various figures unless otherwise specified.

DETAILED DESCRIPTION

Figure 1:
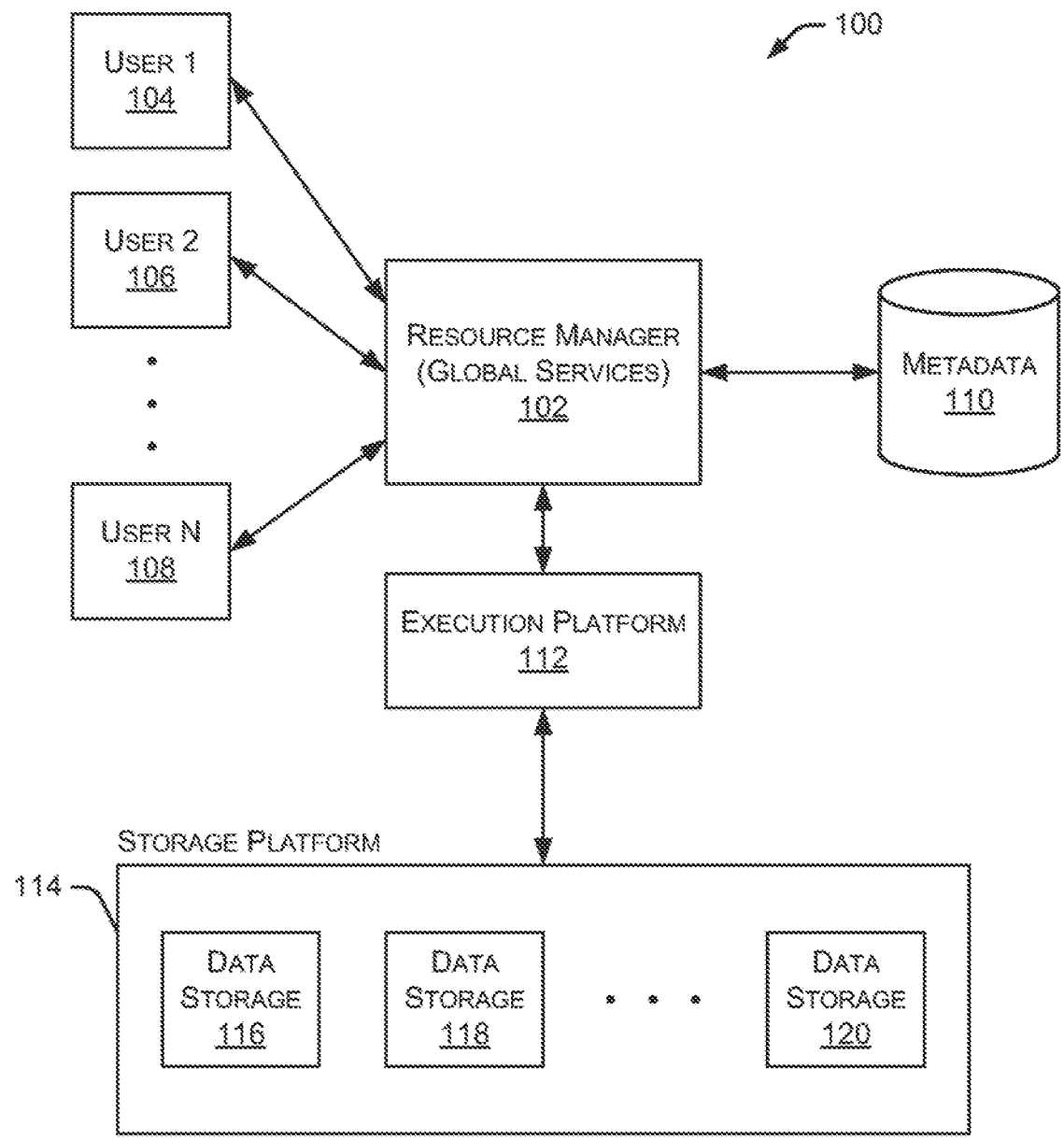
FIG. 1 is a block diagram depicting an example embodiment of the systems and methods described herein.

The systems and methods described herein provide a new platform for storing and retrieving data without the problems faced by existing systems. For example, this new platform supports the addition of new nodes without the need for rearranging data files as required by the shared-nothing architecture. Additionally, nodes can be added to the platform without creating bottlenecks that are common in the shared-disk system. This new platform is always available for data read and data write operations, even when some of the nodes are offline for maintenance or have suffered a failure. The described platform separates the data storage resources from the computing resources so that data can be stored without requiring the use of dedicated computing resources. This is an improvement over the shared-nothing architecture, which fails to store data if all computing resources are removed. Therefore, the new platform continues to store data even though the computing resources are no longer available or are performing other tasks.

As described in more detail below, the described systems and method support the copying of large amounts of data stored in database warehouses. A cloning technique is used to create new objects related to a copy of the data without actually copying the data itself. This cloning technique simplifies the process of updating large batches of data and experimenting with specific sets of data. In particular, the described systems and methods are capable of identifying an original catalog object associated with a set of data and creating a duplicate copy of the original catalog object without copying the data itself. The systems allow access to the set of data in the data storage system using the duplicate catalog object. The data associated with the original catalog object can be modified independently of the duplicate catalog object. After the data associated with the original catalog object has been modified, the system may delete the duplicate catalog object or delete the original catalog object. As discussed herein, example catalog objects include a database instance including metadata that defines database objects such as schemas, tables, views, columns, constraints, sequences, functions, file formats, stages, and the like. Other example catalog objects may contain any type of data or data structures. When discussing various systems and methods, a "catalog object" may also be referred to as a "schema object."

In the following description, reference is made to the accompanying drawings that form a part thereof, and in which is shown by way of illustration specific exemplary embodiments in which the disclosure may be practiced. These embodiments are described in sufficient detail to enable those skilled in the art to practice the concepts disclosed herein, and it is to be understood that modifications to the various disclosed embodiments may be made, and other embodiments may be utilized, without departing from the scope of the present disclosure. The following detailed description is, therefore, not to be taken in a limiting sense.

Reference throughout this specification to "one embodiment," "an embodiment," "one example" or "an example" means that a particular feature, structure or characteristic described in connection with the embodiment or example is included in at least one embodiment of the present disclosure. Thus, appearances of the phrases "in one embodiment," "in an embodiment," "one example" or "an example" in various places throughout this specification are not necessarily all referring to the same embodiment or example. In addition, it should be appreciated that the figures provided herewith are for explanation purposes to persons ordinarily skilled in the art and that the drawings are not necessarily drawn to scale.

Embodiments in accordance with the present disclosure may be embodied as an apparatus, method or computer program product. Accordingly, the present disclosure may take the form of an entirely hardware-comprised embodiment, an entirely software-comprised embodiment (including firmware, resident software, micro-code, etc.) or an embodiment combining software and hardware aspects that may all generally be referred to herein as a "circuit," "module" or "system." Furthermore, embodiments of the present disclosure may take the form of a computer program product embodied in any tangible medium of expression having computer-usable program code embodied in the medium.

Any combination of one or more computer-usable or computer-readable media may be utilized. For example, a computer-readable medium may include one or more of a portable computer diskette, a hard disk, a random access memory (RAM) device, a read-only memory (ROM) device, an erasable programmable read-only memory (EPROM or Flash memory) device, a portable compact disc read-only memory (CDROM), an optical storage device, and a magnetic storage device. Computer program code for carrying out operations of the present disclosure may be written in any combination of one or more programming languages. Such code may be compiled from source code to computer-readable assembly language or machine code suitable for the device or computer on which the code will be executed.

Embodiments may also be implemented in cloud computing environments. In this description and the following claims, "cloud computing" may be defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction and then scaled accordingly. A cloud model can be composed of various characteristics (e.g., on-demand self-service, broad network access, resource pooling, rapid elasticity, and measured service), service models (e.g., Software as a Service ("SaaS"), Platform as a Service ("PaaS"), and Infrastructure as a Service ("IaaS")), and deployment models (e.g., private cloud, community cloud, public cloud, and hybrid cloud).

The flow diagrams and block diagrams in the attached figures illustrate the architecture, functionality, and operation of possible implementations of systems, methods, and computer program products according to various embodiments of the present disclosure. In this regard, each block in the flow diagrams or block diagrams may represent a module, segment, or portion of code, which comprises one or more executable instructions for implementing the specified logical function(s). It will also be noted that each block of the block diagrams and/or flow diagrams, and combinations of blocks in the block diagrams and/or flow diagrams, may be implemented by special purpose hardware-based systems that perform the specified functions or acts, or combinations of special purpose hardware and computer instructions. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flow diagram and/or block diagram block or blocks.

The systems and methods described herein provide a flexible and scalable data warehouse using a new data processing platform. In some embodiments, the described systems and methods leverage a cloud infrastructure that supports cloud-based storage resources, computing resources, and the like. Example cloud-based storage resources offer significant storage capacity available on-demand at a low cost. Further, these cloud-based storage resources may be fault-tolerant and highly scalable, which can be costly to achieve in private data storage systems. Example cloud-based computing resources are available on-demand and may be priced based on actual usage levels of the resources. Typically, the cloud infrastructure is dynamically deployed, reconfigured, and decommissioned in a rapid manner.

In the described systems and methods, a data storage system utilizes an SQL (Structured Query Language)-based relational database. However, these systems and methods are applicable to any type of database, and any type of data storage and retrieval platform, using any data storage architecture and using any language to store and retrieve data within the data storage and retrieval platform. The systems and methods described herein further provide a multi-tenant system that supports isolation of computing resources and data between different customers/clients and between different users within the same customer/client.

FIG. 1 is a block diagram depicting an example embodiment of a new data processing platform 100. As shown in FIG. 1, a resource manager 102 is coupled to multiple users 104, 106, and 108. In particular implementations, resource manager 102 can support any number of users desiring access to data processing platform 100. Users 104-108 may include, for example, end users providing data storage and retrieval requests, system administrators managing the systems and methods described herein, and other components/ devices that interact with resource manager 102. Resource manager 102 provides various services and functions that support the operation of all systems and components within data processing platform 100. As used herein, resource manager 102 may also be referred to as a "global services system" that performs various functions as discussed herein.

Resource manager 102 is also coupled to metadata 110, which is associated with the entirety of data stored throughout data processing platform 100. In some embodiments, metadata 110 includes a catalog of data stored in remote data storage systems as well as data available from a local cache. In particular embodiments, the catalog of data stored in the remote data storage systems includes a summary of data stored in the remote data storage systems. Additionally, metadata 110 may include information regarding how data is organized in the remote data storage systems and the local caches. Metadata 110 allows systems and services to determine whether a piece of data needs to be accessed without loading or accessing the actual data from a storage device.

Resource manager 102 is further coupled to an execution platform 112, which provides multiple computing resources that execute various data storage and data retrieval tasks, as discussed in greater detail below. Execution platform 112 is coupled to multiple data storage devices 116, 118, and 120 that are part of a storage platform 114. Although three data storage devices 116, 118, and 120 are shown in FIG. 1, execution platform 112 is capable of communicating with any number of data storage devices. In some embodiments, data storage devices 116, 118, and 120 are cloud-based storage devices located in one or more geographic locations. For example, data storage devices 116, 118, and 120 may be part of a public cloud infrastructure or a private cloud infrastructure. Data storage devices 116, 118, and 120 may be hard disk drives (HDDs), solid state drives (SSDs), storage clusters, Amazon S3™ storage systems or any other data storage technology. Additionally, storage platform 114 may include distributed file systems (such as Hadoop Distributed File Systems (HDFS)), object storage systems, and the like.

In particular embodiments, the communication links between resource manager 102 and users 104-108, metadata 110, and execution platform 112 are implemented via one or more data communication networks. Similarly, the communication links between execution platform 112 and data storage devices 116-120 in storage platform 114 are implemented via one or more data communication networks. These data communication networks may utilize any communication protocol and any type of communication medium. In some embodiments, the data communication networks are a combination of two or more data communication networks (or sub-networks) coupled to one another. In alternate embodiments, these communication links are implemented using any type of communication medium and any communication protocol.

As shown in FIG. 1, data storage devices 116, 118, and 120 are decoupled from the computing resources associated with execution platform 112. This architecture supports dynamic changes to data processing platform 100 based on the changing data storage/retrieval needs as well as the changing needs of the users and systems accessing data processing platform 100. The support of dynamic changes allows data processing platform 100 to scale quickly in response to changing demands on the systems and components within data processing platform 100. The decoupling of the computing resources from the data storage devices supports the storage of large amounts of data without requiring a corresponding large amount of computing resources. Similarly, this decoupling of resources supports a significant increase in the computing resources utilized at a particular time without requiring a corresponding increase in the available data storage resources.

Resource manager 102, metadata 110, execution platform 112, and storage platform 114 are shown in FIG. 1 as individual components. However, each of resource manager 102, metadata 110, execution platform 112, and storage platform 114 may be implemented as a distributed system (e.g., distributed across multiple systems/platforms at multiple geographic locations). Additionally, each of resource manager 102, metadata 110, execution platform 112, and storage platform 114 can be scaled up or down (independently of one another) depending on changes to the requests received from users 104-108 and the changing needs of data processing platform 100. Thus, in the described embodiments, data processing platform 100 is dynamic and supports regular changes to meet the current data processing needs.

During typical operation, data processing platform 100 processes multiple queries (or requests) received from any of the users 104-108. These queries are managed by resource manager 102 to determine when and how to execute the queries. For example, resource manager 102 may determine what data is needed to process the query and further determine which nodes within execution platform 112 are best suited to process the query. Some nodes may have already cached the data needed to process the query and, therefore, are good candidates for processing the query. Metadata 110 assists resource manager 102 in determining which nodes in execution platform 112 already cache at least a portion of the data needed to process the query. One or more nodes in execution platform 112 process the query using data cached by the nodes and, if necessary, data retrieved from storage platform 114. It is desirable to retrieve as much data as possible from caches within execution platform 112 because the retrieval speed is typically much faster than retrieving data from storage platform 114.

As shown in FIG. 1, data processing platform 100 separates execution platform 112 from storage platform 114. In this arrangement, the processing resources and cache resources in execution platform 112 operate independently of the data storage resources 116-120 in storage platform 114. Thus, the computing resources and cache resources are not restricted to specific data storage resources 116-120. Instead, all computing resources and all cache resources may retrieve data from, and store data to, any of the data storage resources in storage platform 114. Additionally, data processing platform 100 supports the addition of new computing resources and cache resources to execution platform 112 without requiring any changes to storage platform 114. Similarly, data processing platform 100 supports the addition of data storage resources to storage platform 114 without requiring any changes to nodes in execution platform 112.

Figure 2:
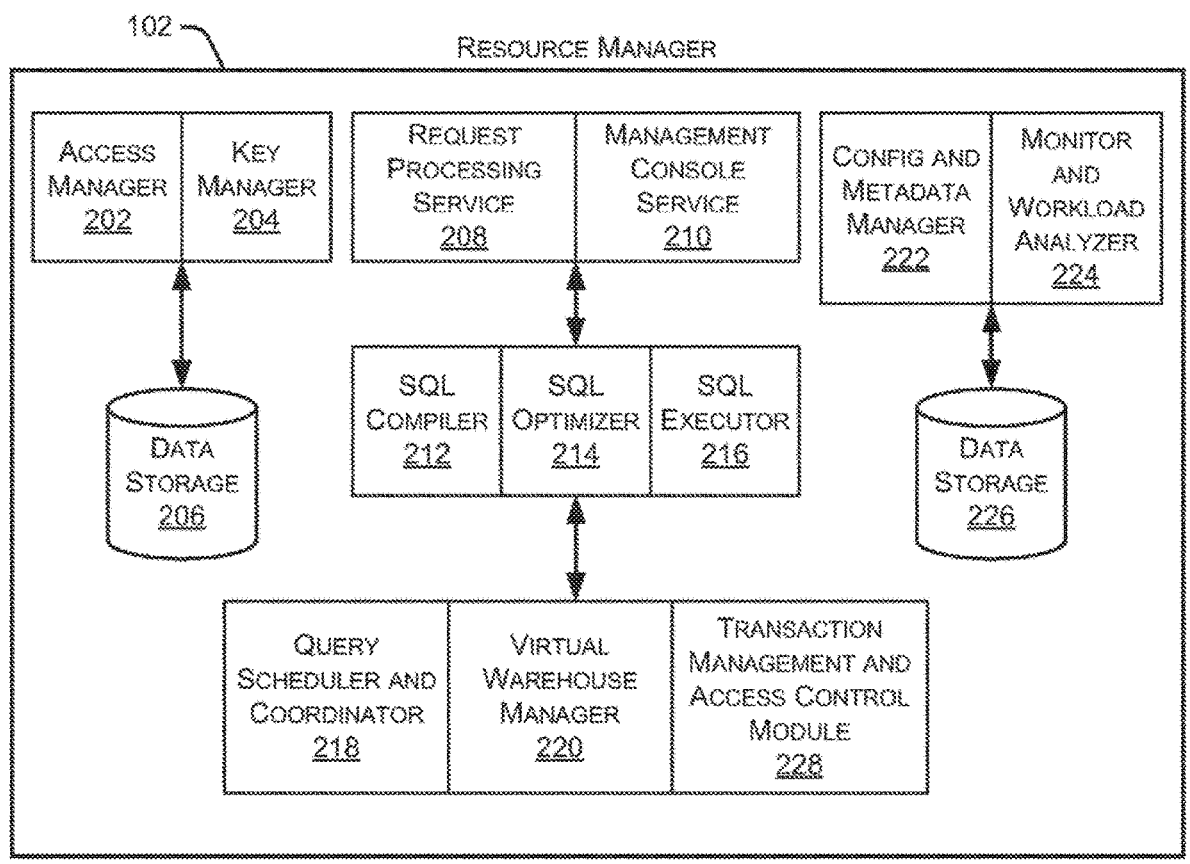
FIG. 2 is a block diagram depicting an embodiment of a resource manager.

FIG. 2 is a block diagram depicting an embodiment of resource manager 102. As shown in FIG. 2, resource manager 102 includes an access manager 202 and a key manager 204 coupled to a data storage device 206. Access manager 202 handles authentication and authorization tasks for the systems described herein. Key manager 204 manages storage and authentication of keys used during authentication and authorization tasks. For example, access manager 202 and key manager 204 manage the keys used to access data stored in remote storage devices (e.g., data storage devices in storage platform 114). As used herein, the remote storage devices may also be referred to as "persistent storage devices." A request processing service 208 manages received data storage requests and data retrieval requests (e.g., database queries). For example, request processing service 208 may determine the data necessary to process the received data storage request or data retrieval request. The necessary data may be stored in a cache within execution platform 112 (as discussed in greater detail below) or in a data storage device in storage platform 114. A management console service 210 supports access to various systems and processes by administrators and other system managers. Additionally, management console service 210 may receive requests from users 104-108 to issue queries and monitor the workload on the system. In some embodiments, a particular user may issue a request to monitor the workload that their specific query places on the system.

Resource manager 102 also includes an SQL compiler 212, an SQL optimizer 214 and an SQL executor 210. SQL compiler 212 parses SQL queries and generates the execution code for the queries. SQL optimizer 214 determines the best method to execute queries based on the data that needs to be processed. SQL optimizer 214 also handles various data pruning operations and other data optimization techniques to improve the speed and efficiency of executing the SQL query. SQL executor 216 executes the query code for queries received by resource manager 102.

A query scheduler and coordinator 218 sends received queries to the appropriate services or systems for compilation, optimization, and dispatch to execution platform 112. For example, queries may be prioritized and processed in that prioritized order. In some embodiments, query scheduler and coordinator 218 identifies or assigns particular nodes in execution platform 112 to process particular queries. A virtual warehouse manager 220 manages the operation of multiple virtual warehouses implemented in execution platform 112. As discussed below, each virtual warehouse includes multiple execution nodes that each include a cache and a processor.

Additionally, resource manager 102 includes a configuration and metadata manager 222, which manages the information related to the data stored in the remote data storage devices and in the local caches (i.e., the caches in execution platform 112). As discussed in greater detail below, configuration and metadata manager 222 uses the metadata to determine which data files need to be accessed to retrieve data for processing a particular query. A monitor and workload analyzer 224 oversees the processes performed by resource manager 102 and manages the distribution of tasks (e.g., workload) across the virtual warehouses and execution nodes in execution platform 112. Monitor and workload analyzer 224 also redistributes tasks, as needed, based on changing workloads throughout data processing platform 100. Configuration and metadata manager 222 and monitor and workload analyzer 224 are coupled to a data storage device 226. Data storage devices 206 and 226 in FIG. 2 represent any data storage device within data processing platform 100. For example, data storage devices 206 and 226 may represent caches in execution platform 112, storage devices in storage platform 114, or any other storage device.

Resource manager 102 also includes a transaction management and access control module 228, which manages the various tasks and other activities associated with the processing of data storage requests and data access requests. For example, transaction management and access control module 228 provides consistent and synchronized access to data by multiple users or systems. Since multiple users/systems may access the same data simultaneously, changes to the data must be synchronized to ensure that each user/system is working with the current version of the data. Transaction management and access control module 228 provides control of various data processing activities at a single, centralized location in resource manager 102. In some embodiments, transaction management and access control module 228 interacts with SQL executor 216 to support the management of various tasks being executed by SQL executor 216.

Figure 3:
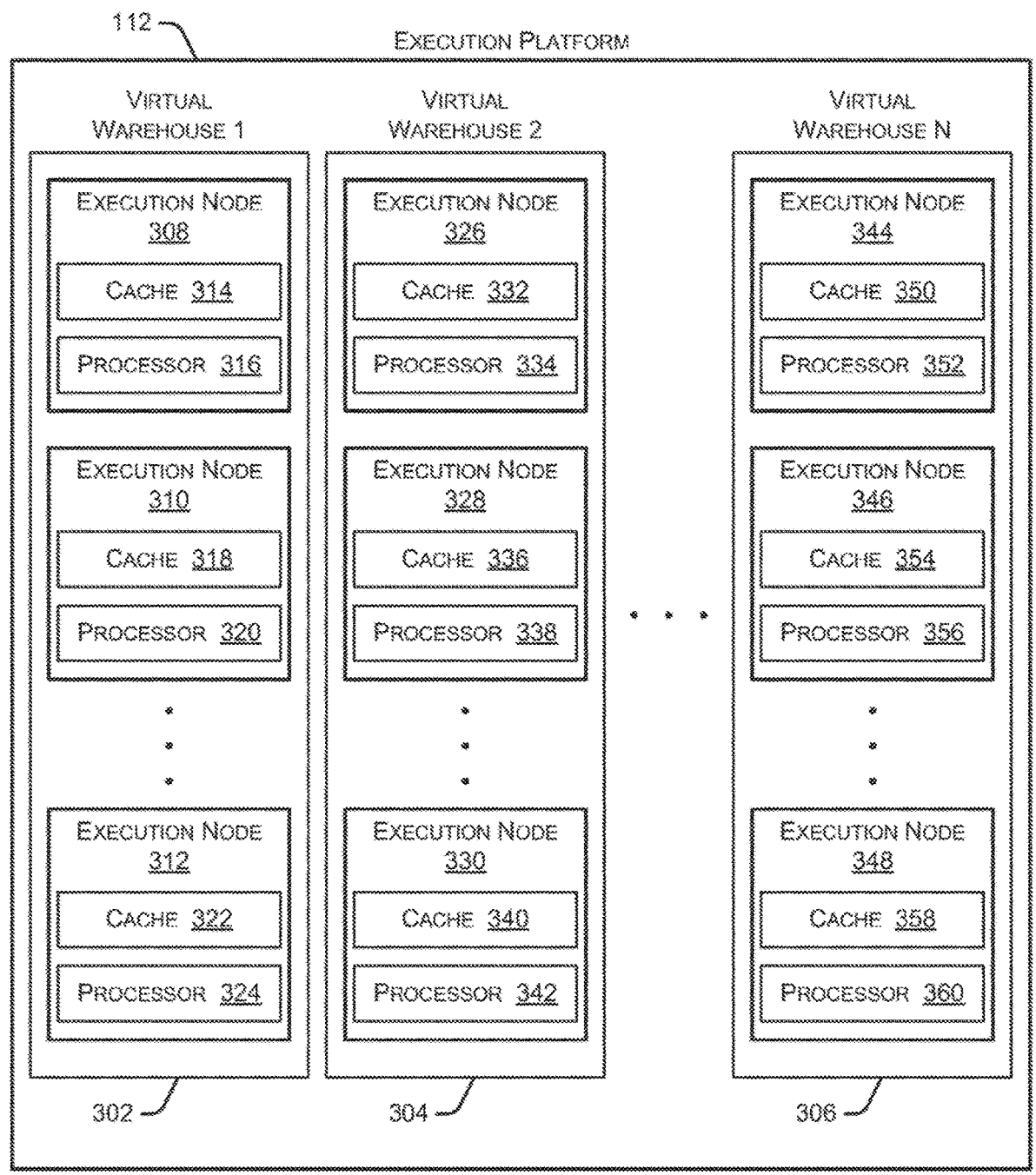
FIG. 3 is a block diagram depicting an embodiment of an execution platform.

FIG. 3 is a block diagram depicting an embodiment of an execution platform 112. As shown in FIG. 3, execution platform 112 includes multiple virtual warehouses 302, 304, and 306. Each virtual warehouse includes multiple execution nodes that each include a data cache and a processor. Virtual warehouses 302, 304, and 306 are capable of executing multiple queries (and other tasks) in parallel by using the multiple execution nodes. As discussed herein, execution platform 112 can add new virtual warehouses and drop existing virtual warehouses in real time based on the current processing needs of the systems and users. This flexibility allows execution platform 112 to quickly deploy large amounts of computing resources when needed without being forced to continue paying for those computing resources when they are no longer needed. All virtual warehouses can access data from any data storage device (e.g., any storage device in storage platform 114).

Although each virtual warehouse 302-306 shown in FIG. 3 includes three execution nodes, a particular virtual warehouse may include any number of execution nodes. Further, the number of execution nodes in a virtual warehouse is dynamic, such that new execution nodes are created when additional demand is present, and existing execution nodes are deleted when they are no longer necessary.

Each virtual warehouse 302-306 is capable of accessing any of the data storage devices 116-120 shown in FIG. 1. Thus, virtual warehouses 302-306 are not necessarily assigned to a specific data storage device 116-120 and, instead, can access data from any of the data storage devices 116-120. Similarly, each of the execution nodes shown in FIG. 3 can access data from any of the data storage devices 116-120. In some embodiments, a particular virtual warehouse or a particular execution node may be temporarily assigned to a specific data storage device, but the virtual warehouse or execution node may later access data from any other data storage device.

In the example of FIG. 3, virtual warehouse 302 includes three execution nodes 308, 310, and 312. Execution node 308 includes a cache 314 and a processor 316. Execution node 310 includes a cache 318 and a processor 320. Execution node 312 includes a cache 322 and a processor 324. Each execution node 308-312 is associated with processing one or more data storage and/or data retrieval tasks. For example, a particular virtual warehouse may handle data storage and data retrieval tasks associated with a particular user or customer. In other implementations, a particular virtual warehouse may handle data storage and data retrieval tasks associated with a particular data storage system or a particular category of data.

Similar to virtual warehouse 302 discussed above, virtual warehouse 304 includes three execution nodes 326, 328, and 330. Execution node 326 includes a cache 332 and a processor 334. Execution node 328 includes a cache 336 and a processor 338. Execution node 330 includes a cache 340 and a processor 342. Additionally, virtual warehouse 306 includes three execution nodes 344, 346, and 348. Execution node 344 includes a cache 350 and a processor 352. Execution node 346 includes a cache 354 and a processor 356. Execution node 348 includes a cache 358 and a processor 360.

In some embodiments, the execution nodes shown in FIG. 3 are stateless with respect to the data the execution nodes are caching. For example, these execution nodes do not store or otherwise maintain state information about the execution node or the data being cached by a particular execution node. Thus, in the event of an execution node failure, the failed node can be transparently replaced by another node. Since there is no state information associated with the failed execution node, the new (replacement) execution node can easily replace the failed node without concern for recreating a particular state.

Although the execution nodes shown in FIG. 3 each include one data cache and one processor, alternate embodiments may include execution nodes containing any number of processors and any number of caches. Additionally, the caches may vary in size among the different execution nodes. The caches shown in FIG. 3 store, in the local execution node, data that was retrieved from one or more data storage devices in storage platform 114 (FIG. 1). Thus, the caches reduce or eliminate the bottleneck problems occurring in platforms that consistently retrieve data from remote storage systems. Instead of repeatedly accessing data from the remote storage devices, the systems and methods described herein access data from the caches in the execution nodes which is significantly faster and avoids the bottleneck problem discussed above. In some embodiments, the caches are implemented using high-speed memory devices that provide fast access to the cached data. Each cache can store data from any of the storage devices in storage platform 114.

Further, the cache resources and computing resources may vary between different execution nodes. For example, one execution node may contain significant computing resources and minimal cache resources, making the execution node useful for tasks that require significant computing resources. Another execution node may contain significant cache resources and minimal computing resources, making this execution node useful for tasks that require caching of large amounts of data. Yet another execution node may contain cache resources providing faster input-output operations, useful for tasks that require fast scanning of large amounts of data. In some embodiments, the cache resources and computing resources associated with a particular execution node are determined when the execution node is created, based on the expected tasks to be performed by the execution node.

Additionally, the cache resources and computing resources associated with a particular execution node may change over time based on changing tasks performed by the execution node. For example, a particular execution node may be assigned more processing resources if the tasks performed by the execution node become more processor intensive. Similarly, an execution node may be assigned more cache resources if the tasks performed by the execution node require a larger cache capacity.

Although virtual warehouses 302-306 are associated with the same execution platform 112, the virtual warehouses may be implemented using multiple computing systems at multiple geographic locations. For example, virtual warehouse 302 can be implemented by a computing system at a first geographic location, while virtual warehouses 304 and 306 are implemented by another computing system at a second geographic location. In some embodiments, these different computing systems are cloud-based computing systems maintained by one or more different entities.

Additionally, each virtual warehouse is shown in FIG. 3 as having multiple execution nodes. The multiple execution nodes associated with each virtual warehouse may be implemented using multiple computing systems at multiple geographic locations. For example, a particular instance of virtual warehouse 302 implements execution nodes 308 and 310 on one computing platform at a particular geographic location, and implements execution node 312 at a different computing platform at another geographic location. Selecting particular computing systems to implement an execution node may depend on various factors, such as the level of resources needed for a particular execution node (e.g., processing resource requirements and cache requirements), the resources available at particular computing systems, communication capabilities of networks within a geographic location or between geographic locations, and which computing systems are already implementing other execution nodes in the virtual warehouse.

Execution platform 112 is also fault tolerant. For example, if one virtual warehouse fails, that virtual warehouse is quickly replaced with a different virtual warehouse at a different geographic location.

A particular execution platform 112 may include any number of virtual warehouses 302-306. Additionally, the number of virtual warehouses in a particular execution platform is dynamic, such that new virtual warehouses are created when additional processing and/or caching resources are needed. Similarly, existing virtual warehouses may be deleted when the resources associated with the virtual warehouse are no longer necessary.

In some embodiments, virtual warehouses 302, 304, and 306 may operate on the same data in storage platform 114, but each virtual warehouse has its own execution nodes with independent processing and caching resources. This configuration allows requests on different virtual warehouses to be processed independently and with no interference between the requests. This independent processing, combined with the ability to dynamically add and remove virtual warehouses, supports the addition of new processing capacity for new users without impacting the performance observed by the existing users.

Figure 4:
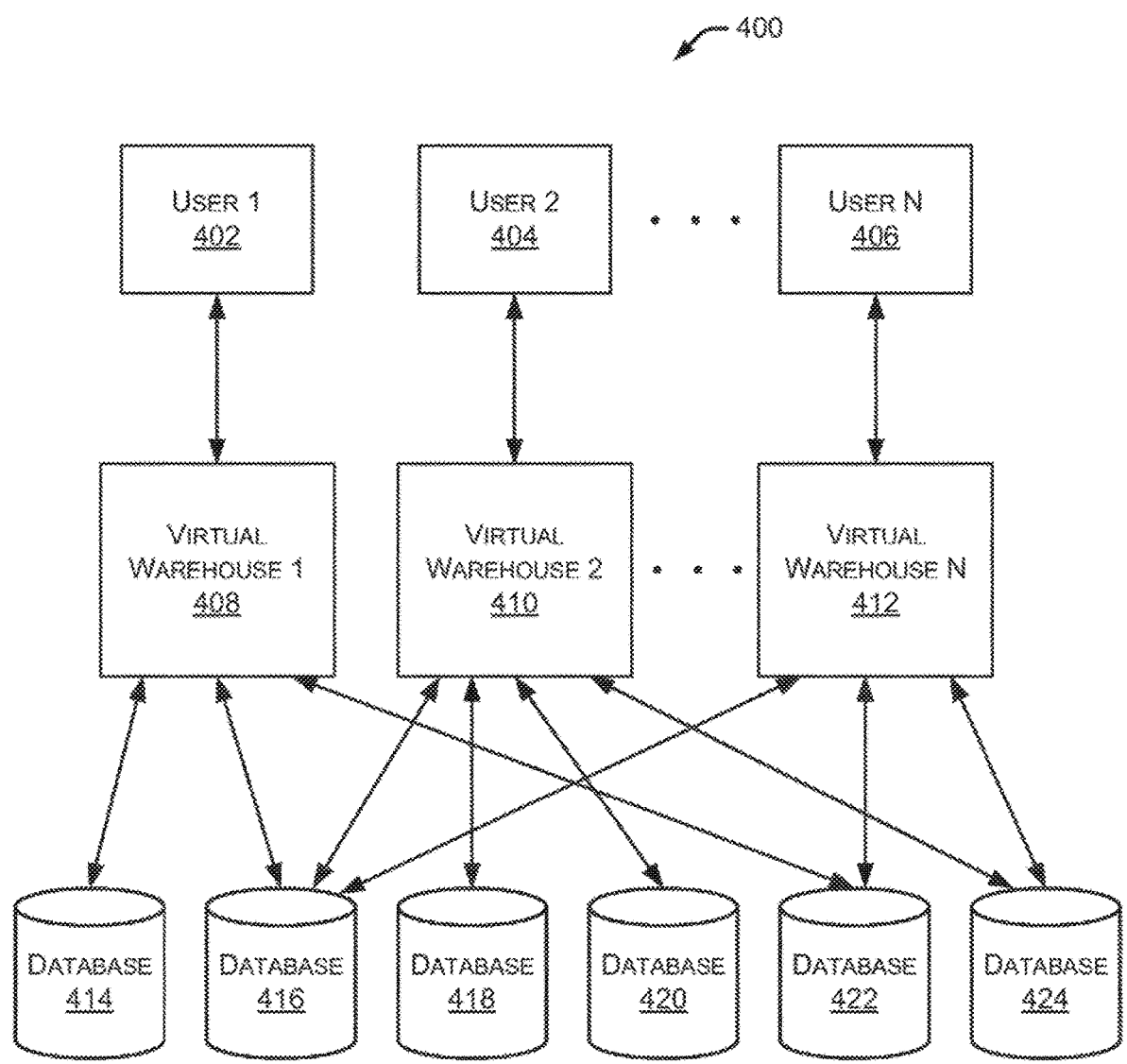
FIG. 4 is a block diagram depicting an example operating environment with multiple users accessing multiple databases through multiple virtual warehouses.

FIG. 4 is a block diagram depicting an example operating environment 400 with multiple users accessing multiple databases through multiple virtual warehouses. In environment 400, multiple users 402, 404, and 406 access multiple databases 414, 416, 418, 420, 422, and 424 through multiple virtual warehouses 408, 410, and 412. Although not shown in FIG. 4, users 402, 404, and 406 may access virtual warehouses 408, 410, and 412 through resource manager 102 (FIG. 1). In particular embodiments, databases 414-424 are contained in storage platform 114 (FIG. 1) and are accessible by any virtual warehouse implemented in execution platform 112. In some embodiments, users 402-406 access one of the virtual warehouses 408-412 using a data communication network, such as the Internet. In some implementations, each user 402-406 specifies a particular virtual warehouse 408-412 to work with at a specific time. In the example of FIG. 4, user 402 interacts with virtual warehouse 408, user 404 interacts with virtual warehouse 410, and user 406 interacts with virtual warehouse 412. Thus, user 402 submits data retrieval and data storage requests through virtual warehouse 408. Similarly, users 404 and 406 submit data retrieval and data storage requests through virtual warehouses 410 and 412, respectively.

Each virtual warehouse 408-412 is configured to communicate with a subset of all databases 414-424. For example, in environment 400, virtual warehouse 408 is configured to communicate with databases 414, 416, and 422. Similarly, virtual warehouse 410 is configured to communicate with databases 416, 418, 420, and 424. And, virtual warehouse 412 is configured to communicate with databases 416, 422, and 424. In alternate embodiments, one or more of virtual warehouses 408-412 communicate with all of the databases 414-424. The arrangement shown in FIG. 4 allows individual users to send all data retrieval and data storage requests through a single virtual warehouse. That virtual warehouse processes the data retrieval and data storage tasks using cached data within one of the execution nodes in the virtual warehouse, or retrieves (and caches) the necessary data from an appropriate database. The mappings between the virtual warehouses is a logical mapping, not a hardware mapping. This logical mapping is based on access control parameters related to security and resource access management settings. The logical mappings are easily changed without requiring reconfiguration of the virtual warehouse or storage resources.

Although environment 400 shows virtual warehouses 408-412 configured to communicate with specific subsets of databases 414-424, that configuration is dynamic. For example, virtual warehouse 408 may be reconfigured to communicate with a different subset of databases 414-424 based on changing tasks to be performed by virtual warehouse 408. For instance, if virtual warehouse 408 receives requests to access data from database 418, virtual warehouse 408 may be reconfigured to also communicate with database 418. If, at a later time, virtual warehouse 408 no longer needs to access data from database 418, virtual warehouse 408 may be reconfigured to delete the communication with database 418.

Figure 5:
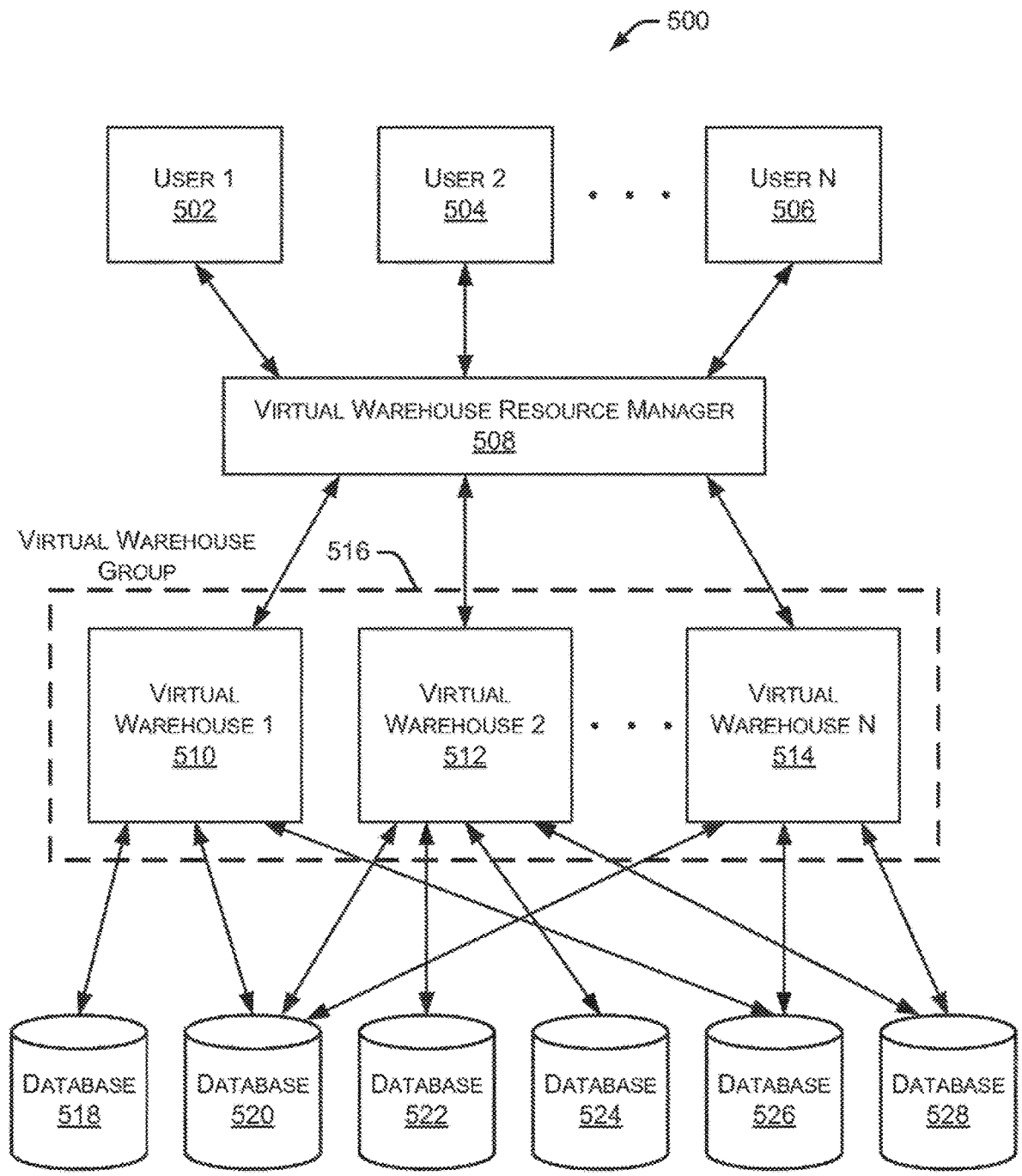
FIG. 5 is a block diagram depicting another example operating environment with multiple users accessing multiple databases through a load balancer and multiple virtual warehouses contained in a virtual warehouse group.

FIG. 5 is a block diagram depicting another example operating environment 500 with multiple users accessing multiple databases through a load balancer and multiple virtual warehouses contained in a virtual warehouse group. Environment 500 is similar to environment 400 (FIG. 4), but additionally includes a virtual warehouse resource manager 508 and multiple virtual warehouses 510, 512, and 514 arranged in a virtual warehouse group 516. Virtual warehouse resource manager 508 may be contained in resource manager 102. In particular, multiple users 502, 504, and 506 access multiple databases 518, 520, 522, 524, 526, and 528 through virtual warehouse resource manager 508 and virtual warehouse group 516. In some embodiments, users 502-506 access virtual warehouse resource manager 508 using a data communication network, such as the Internet. Although not shown in FIG. 5, users 502, 504, and 506 may access virtual warehouse resource manager 508 through resource manager 102 (FIG. 1). In some embodiments, virtual warehouse resource manager 508 is implemented within resource manager 102.

Users 502-506 may submit data retrieval and data storage requests to virtual warehouse resource manager 508, which routes the data retrieval and data storage requests to an appropriate virtual warehouse 510-514 in virtual warehouse group 516. In some implementations, virtual warehouse resource manager 508 provides a dynamic assignment of users 502-506 to virtual warehouses 510-514. When submitting a data retrieval or data storage request, users 502-506 may specify virtual warehouse group 516 to process the request without specifying the particular virtual warehouse 510-514 that will process the request. This arrangement allows virtual warehouse resource manager 508 to distribute multiple requests across the virtual warehouses 510-514 based on efficiency, available resources, and the availability of cached data within the virtual warehouses 510-514. When determining how to route data processing requests, virtual warehouse resource manager 508 considers available resources, current resource loads, number of current users, and the like.

In some embodiments, fault tolerance systems create a new virtual warehouses in response to a failure of a virtual warehouse. The new virtual warehouse may be in the same virtual warehouse group or may be created in a different virtual warehouse group at a different geographic location.

Each virtual warehouse 510-514 is configured to communicate with a subset of all databases 518-528. For example, in environment 500, virtual warehouse 510 is configured to communicate with databases 518, 520, and 526. Similarly, virtual warehouse 512 is configured to communicate with databases 520, 522, 524, and 528. And, virtual warehouse 514 is configured to communicate with databases 520, 526, and 528. In alternate embodiments, virtual warehouses 510-514 may communicate with any (or all) of the databases 518-528.

Although environment 500 shows one virtual warehouse group 516, alternate embodiments may include any number of virtual warehouse groups, each associated with any number of virtual warehouses. The number of virtual warehouse groups in a particular environment is dynamic and may change based on the changing needs of the users and other systems in the environment.

Figure 6:
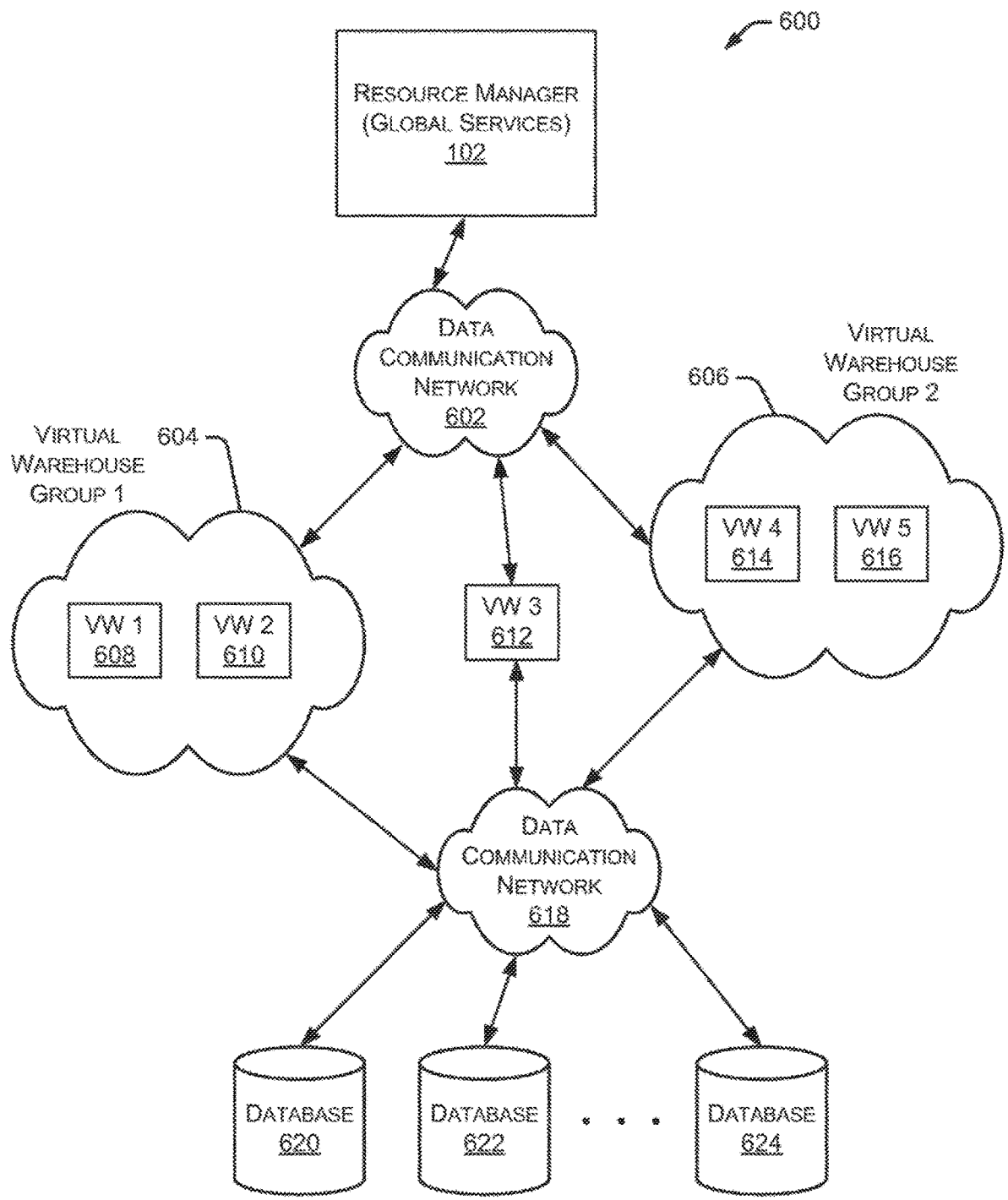
FIG. 6 is a block diagram depicting another example operating environment having multiple distributed virtual warehouses and virtual warehouse groups.

FIG. 6 is a block diagram depicting another example operating environment 600 having multiple distributed virtual warehouses and virtual warehouse groups. Environment 600 includes resource manager 102 that communicates with virtual warehouse groups 604 and 606 through a data communication network 602. Warehouse group 604 includes two virtual warehouses 608 and 610, and warehouse group 606 includes another two virtual warehouses 614 and 616. Resource manager 102 also communicates with virtual warehouse 612 (which is not part of a virtual warehouse group) through data communication network 602.

Virtual warehouse groups 604 and 606 as well as virtual warehouse 612 communicate with databases 620, 622, and 624 through a data communication network 618. In some embodiments data communication networks 602 and 618 are the same network. Environment 600 allows resource manager 102 to coordinate user data storage and retrieval requests across the multiple virtual warehouses 608-616 to store and retrieve data in databases 620-624. Virtual warehouse groups 604 and 606 can be located in the same geographic area, or can be separated geographically. Additionally, virtual warehouse groups 604 and 606 can be implemented by the same entity or by different entities.

The systems and methods described herein allow data to be stored and accessed as a service that is separate from computing (or processing) resources. Even if no computing resources have been allocated from the execution platform, data is available to a virtual warehouse without requiring reloading of the data from a remote data source. Thus, data is available independently of the allocation of computing resources associated with the data. The described systems and methods are useful with any type of data. In particular embodiments, data is stored in a structured, optimized format. The decoupling of the data storage/access service from the computing services also simplifies the sharing of data among different users and groups. As discussed herein, each virtual warehouse can access any data to which it has access permissions, even at the same time as other virtual warehouses are accessing the same data. This architecture supports running queries without any actual data stored in the local cache. The systems and methods described herein are capable of transparent dynamic data movement, which moves data from a remote storage device to a local cache, as needed, in a manner that is transparent to the user of the system. Further, this architecture supports data sharing without prior data movement since any virtual warehouse can access any data due to the decoupling of the data storage service from the computing service.

Figure 7:
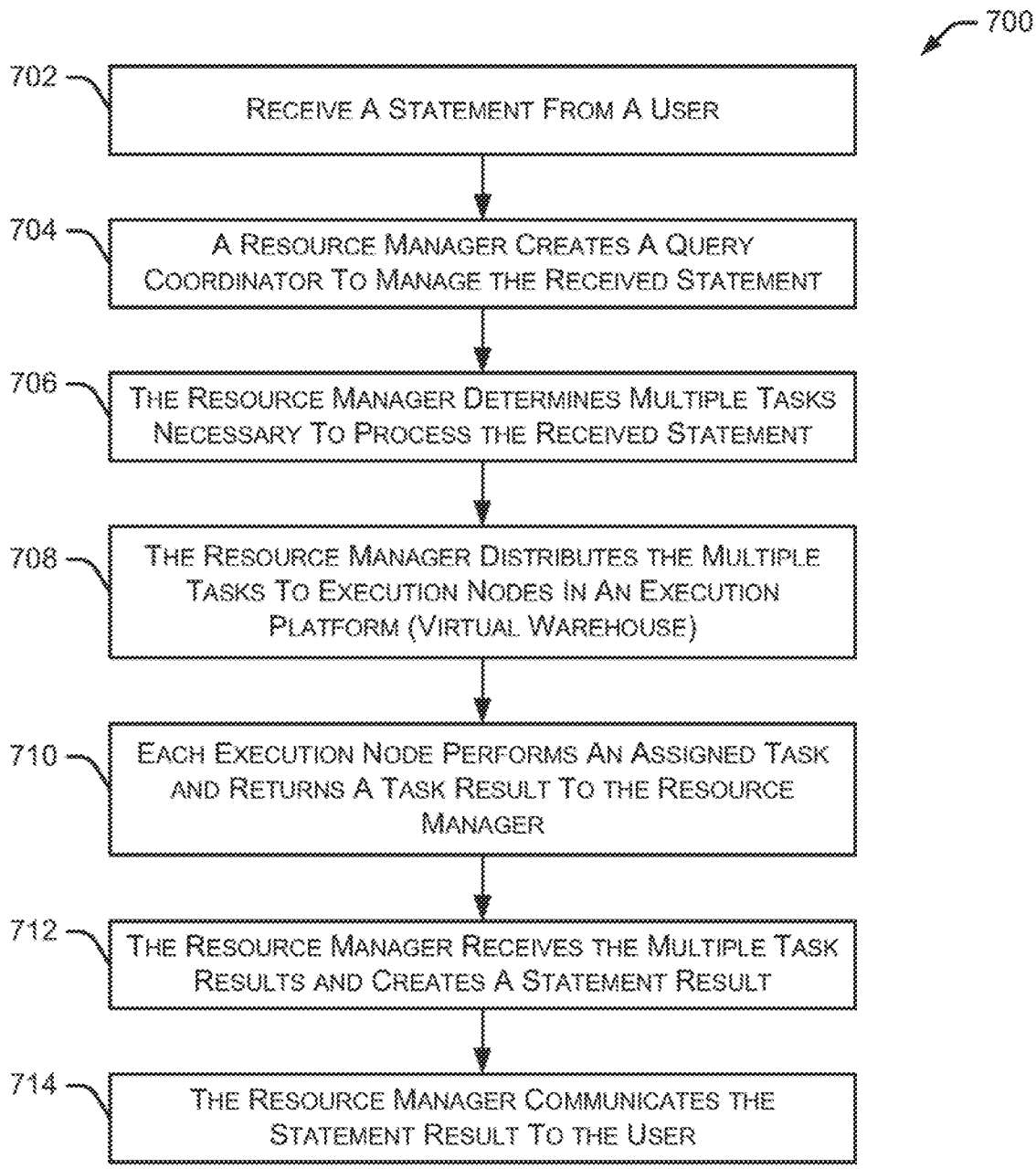
FIG. 7 is a flow diagram depicting an embodiment of a method for managing data storage and retrieval operations.

FIG. 7 is a flow diagram depicting an embodiment of a method 700 for managing data storage and retrieval operations. Initially, method 700 receives a statement, request or query from a user at 702. A statement is any request or command to perform a data-related operation. Example statements include data retrieval requests, data storage requests, data transfer requests, data queries, and the like. In some embodiments, the statement is implemented as an SQL statement. A resource manager creates a query coordinator at 704 to manage the received statement. For example, the query coordinator manages the various tasks necessary to process the received statement, including interacting with an execution platform and one or more data storage devices. In some embodiments, the query coordinator is a temporary routine created specifically to manage the received statement.

Method 700 continues as the resource manager determines multiple tasks necessary to process the received statement at 706. The multiple tasks may include, for example, accessing data from a cache in an execution node, retrieving data from a remote storage device, updating data in a cache, storing data in a remote storage device, and the like. The resource manager also distributes the multiple tasks to execution nodes in the execution platform at 708. As discussed herein, the execution nodes in the execution platform are implemented within virtual warehouses. Each execution node performs an assigned task and returns a task result to the resource manager at 710. In some embodiments, the execution nodes return the task results to the query coordinator. The resource manager receives the multiple task results and creates a statement result at 712, and communicates the statement result to the user at 714. In some embodiments, the query coordinator is deleted after the statement result is communicated to the user.

In some implementations, the same file is cached by multiple execution nodes at the same time. This multiple caching of files helps with load balancing (e.g., balancing data processing tasks) across multiple execution nodes. Additionally, caching a file in multiple execution nodes helps avoid potential bottlenecks when significant amounts of data are trying to pass through the same communication link. This implementation also supports the parallel processing of the same data by different execution nodes.

The systems and methods described herein take advantage of the benefits of both shared-disk systems and the shared-nothing architecture. The described platform for storing and retrieving data is scalable like the shared-nothing architecture once data is cached locally. It also has all the benefits of a shared-disk architecture where processing nodes can be added and removed without any constraints (e.g., for 0 to N) and without requiring any explicit reshuffling of data.

In previous data management systems, copying large amounts of data in a data warehouse was time consuming and required significant resources to maintain and process multiple copies of the same data. Additionally, data inconsistencies exist in these previous systems while the data is being copied and changes are applied to one of the sets of data.

However, the systems and methods described herein for cloning catalog objects generate a new catalog object which is activated quickly and is independent of the original catalog object. As discussed below, the new catalog object is created without duplicating the data associated with the catalog object. Instead, only the metadata associated with the catalog object is copied, which is significantly faster than attempting to copy the data itself. For example, by copying only the metadata associated with a catalog object may be several orders of magnitude faster than copying all of the data. In an example situation, 1 KB of metadata is copied instead of 1 MB of actual data.

As used herein, a table is a logical grouping of data and a schema is a set of tables. Example catalog objects include, for example, a table, a database, a schema, an account, a constraint, a file format, a function, a role, a sequence, a stage, a column, a user, and a volume. The following hierarchy represents an example hierarchy of objects used with the systems and methods described herein.

account—database—schema—table/view/sequence—columns/constraints
    account—database—schema—function/file format/stage
    account—user
    account—role
    account—volume
    account—warehouse In some embodiments, these catalog objects are defined by the SQL standard. As discussed herein, a table contains multiple rows and columns. A schema contains any number of tables, and a database contains any number of schemas. The systems and methods described herein are capable of cloning tables, schemas and databases. In some implementations, individual tables may be cloned, while other implementations may clone entire databases, depending on the data operations being performed. Additionally, a cloning operation may clone all generations of children under a root catalog object. Since a cloned higher level object is independent of the original object, new child catalog objects can be added to the cloned object (or cloned child catalog objects can be removed from the cloned object) without affecting the original higher level object and its hierarchy.

Cloning a catalog object creates a new catalog object of the same type quickly and without creating an additional copy of the data. For example, if a database is being cloned, the cloning process creates a new database object and all the tables and schemas and other catalog objects under that database object, but does not copy the data contained in the database. After the cloning process is finished, the cloned catalog object and the original catalog object can be modified independently of one another. Additionally, objects can be added to and removed from each copy of the catalog object as well as the original catalog object.

Figure 8:
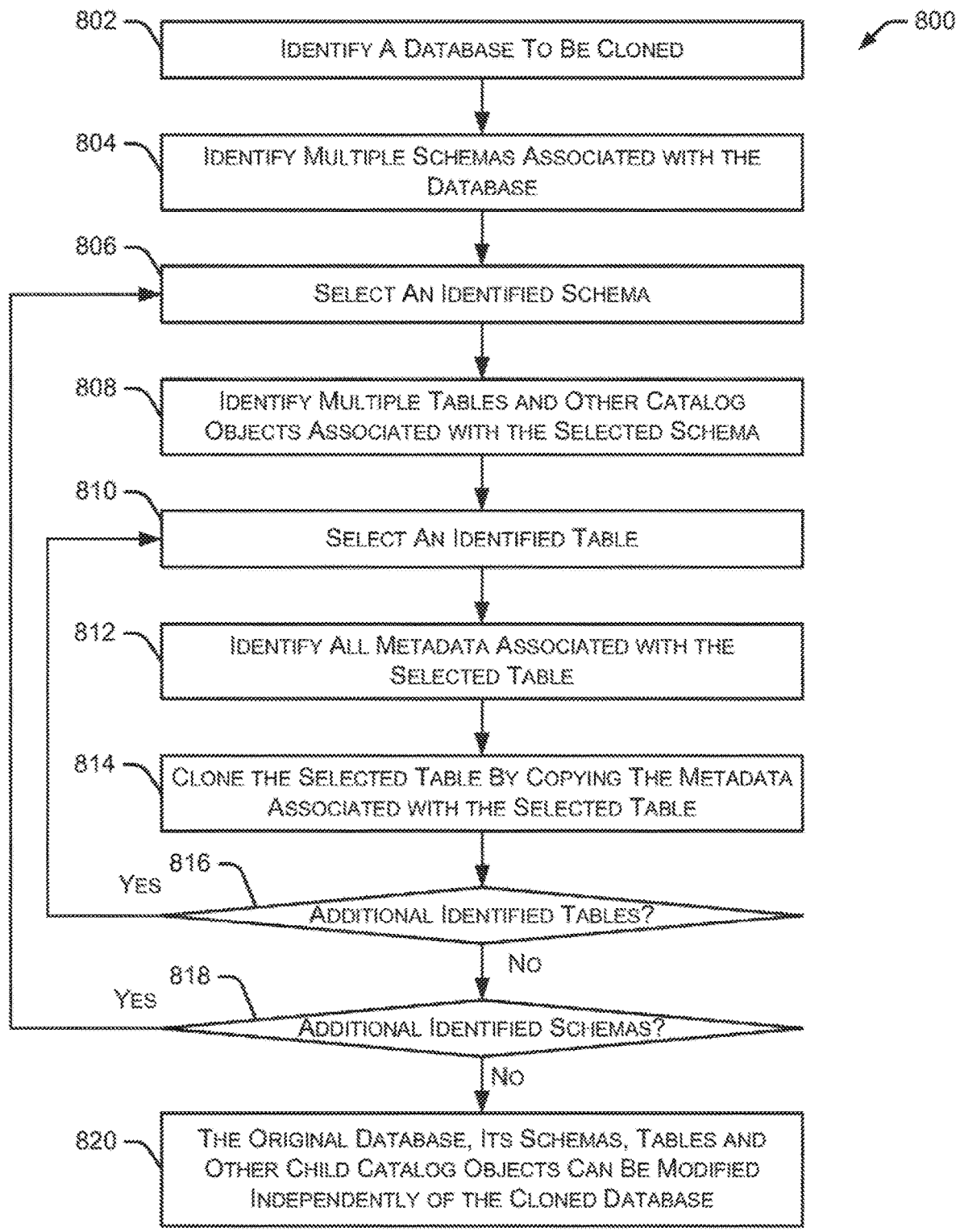
FIG. 8 is a flow diagram depicting an embodiment of a method for cloning catalog objects.

FIG. 8 is a flow diagram depicting an embodiment of a method for cloning catalog objects. Initially, method 800 identifies a database to be cloned at 802. This database may contain any number of schemas. Method 800 continues by identifying multiple schemas associated with the database at 804 and selecting one of the identified schemas at 806. The method then identifies multiple tables and other catalog objects associated with the selected schema at 808. One of the identified tables is selected at 810 and all metadata associated with the selected table is identified at 812. In some embodiments, this metadata includes a summary of data stored in the database. As discussed herein, the metadata may include information regarding how data is organized in the database, tables or other storage mechanisms. The metadata allows the systems and methods discussed herein to determine information about stored data without loading or accessing the actual data from a storage device.

Method 800 clones the selected table at 814 by copying the metadata associated with the selected table. This copying of metadata is performed quickly as compared to the time necessary to copy all of the data associated with the metadata. After the table is cloned at 814, the method determines whether there are additional tables in the selected schema that need to be cloned at 816. If additional tables remain to be cloned, method 800 returns to 810 to select the next table in the schema. If all tables in the selected schema have been cloned, the method determines at 818 whether there are additional schemas in the identified database to be cloned. If additional schemas remain to be cloned, method 800 returns to 806 to select the next schema in the database. This recursive operation ensures that all tables in all schemas of the identified database are cloned. After all schemas in the identified database have been cloned, the original database, its schemas, tables, and other child catalog objects can be modified independently of the cloned database at 820.

In some embodiments, data in the cloned tables is used for current data access requests while data in the original tables is modified. When the modifications of the original tables are complete, the cloned tables are deleted and all data access requests are handled using the original tables. In these embodiments, the copying of metadata without copying the actual underlying data, significantly increases the speed of the data modification process and reduces the additional computing and storage resources necessary to perform the data modification procedure. In some implementations, the data modification procedure is managed my transaction management and access control module 228 (FIG. 2). Additionally, in some embodiments, the metadata is managed by, and accessed through, configuration and metadata manager 222.

Figure 9:
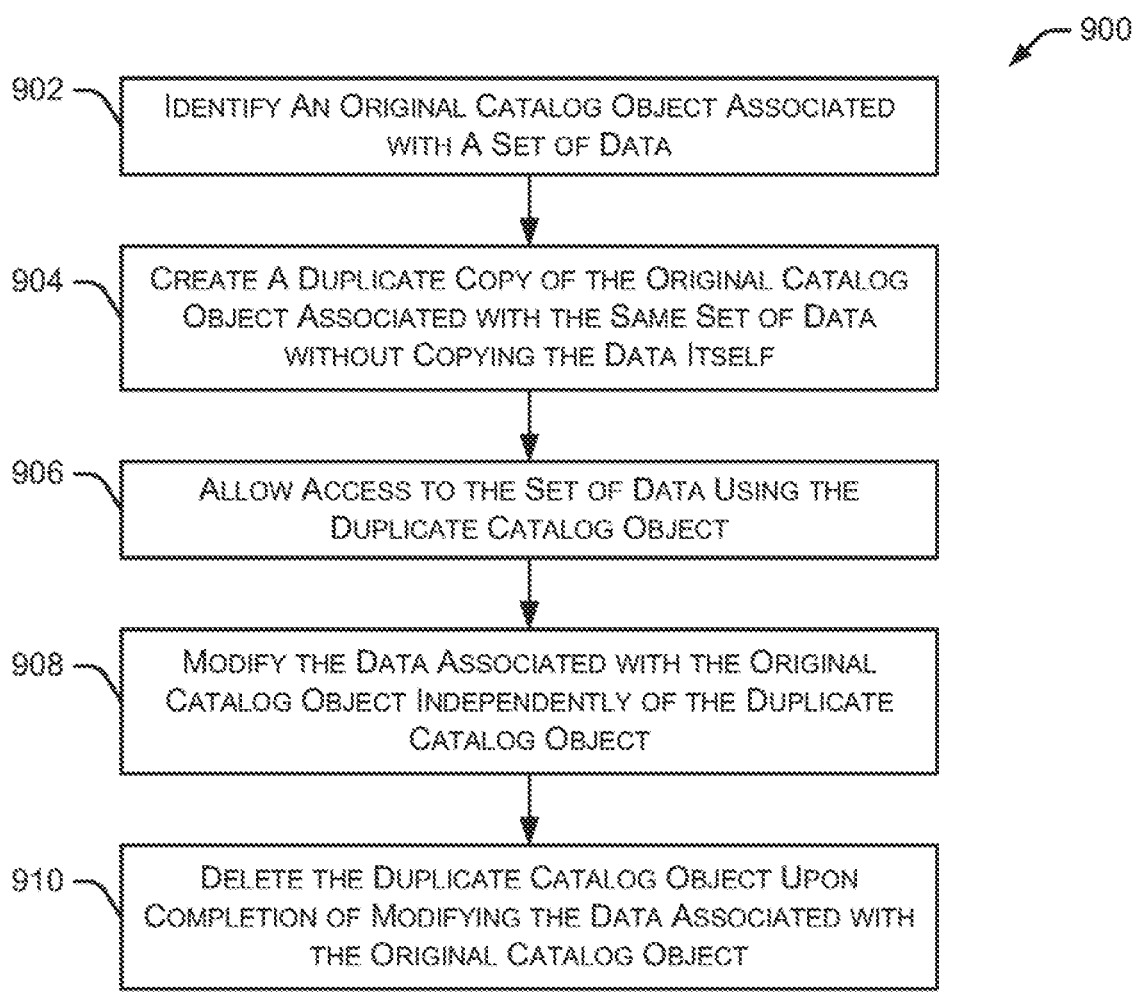
FIG. 9 is a flow diagram depicting an embodiment of a method for creating a temporary duplicate catalog object.

FIG. 9 is a flow diagram depicting an embodiment of a method 900 for creating a temporary duplicate catalog object. Initially, method 900 identifies an original catalog object associated with a set of data at 902. In some embodiments, the original catalog object represents a logical grouping of data in a data storage system. The original catalog object may include one or more of a table, a database, a schema, an account, a constraint, a file format, a function, a role, a sequence, a stage, a column, a user, a volume, or other catalog objects. A duplicate copy of the original catalog object is created at 904 without copying the data itself. In some embodiments, creating the duplicate copy of the original catalog object includes copying metadata associated with the set of data to the duplicate catalog object. This metadata may include an inventory of data stored in the set of data and may identify information regarding the set of data without requiring access to actual data contained in the set of data. In particular implementations, the duplicate catalog object is read only. In some embodiments, the duplicate catalog object includes a duplicate hierarchy of all generations of children.

The method allows access 906 to the set of data using the duplicate catalog object, where the data associated with the original catalog object can be modified independently of the duplicate catalog object at 908. In some embodiments, the modified data associated with the original catalog object is not visible to the duplicate catalog object. Further, the modified data associated with the duplicate catalog object may not be visible to the original catalog object. In other embodiments, data deleted from the original catalog object remains visible to the duplicate catalog object and data deleted from the duplicate catalog object remains visible to the original catalog object. In particular implementations, inserted data associated with the original catalog object is not visible to the duplicate catalog object and inserted data associated with the duplicate catalog object is not visible to the original catalog object. After modification of the data associated with the original catalog object is complete, the duplicate catalog object is deleted at 910. The creation of a duplicate catalog object without copying the data itself can save significant time, bandwidth, and computing resources as compared to making a full copy of the original catalog object including all of the associated data.

FIGS. 10A-10D illustrate the cloning of tables. In the embodiment depicted in FIGS. 10A-10D, each table contains a collection of multiple files. As described below, once a file is written it cannot be updated or modified. If changes to the file are necessary, the file is deleted and replaced with a different file that contains the changes. If a particular file is not in use, it may be deleted. The metadata discussed above may include information regarding the relationship between the table and the files associated with that table. This relationship between the table and the files may also be referred to as a mapping of the files.

Figure 10A:
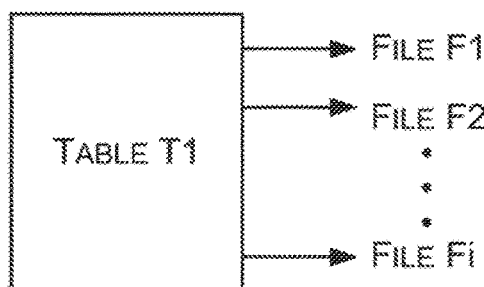
FIGS. 10A-10D depict an embodiment of an original table object and a cloned table object accessing multiple files.
Figure 10B:
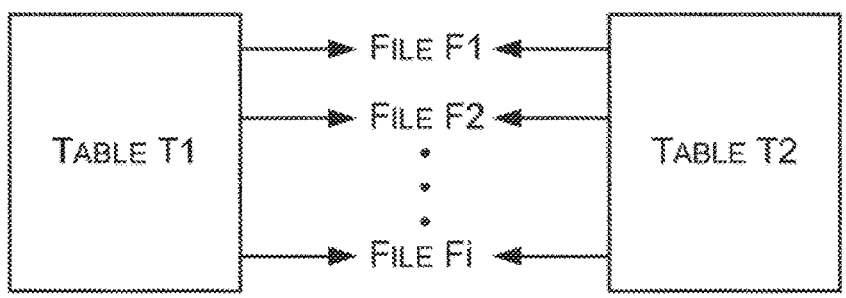

FIG. 10A illustrates an example table T1 with i files (labeled F1, F2 . . . Fi). FIG. 10B shows the result of a cloning of table T1 to create a cloned table T2. In this embodiment, the cloning process copies the metadata from table T1 to the cloned table T2. As discussed herein, copying the metadata is much faster than copying all of the underlying data. FIG. 10B shows that both table T1 and table T2 are associated with the same files immediately after the cloning process.

Figure 10C:
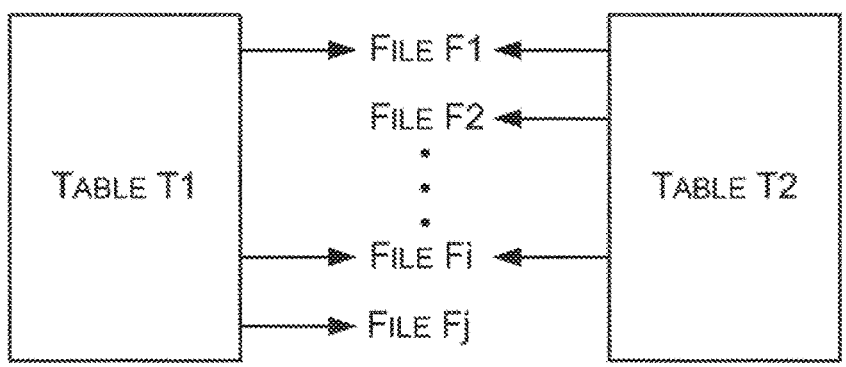
Figure 10D:
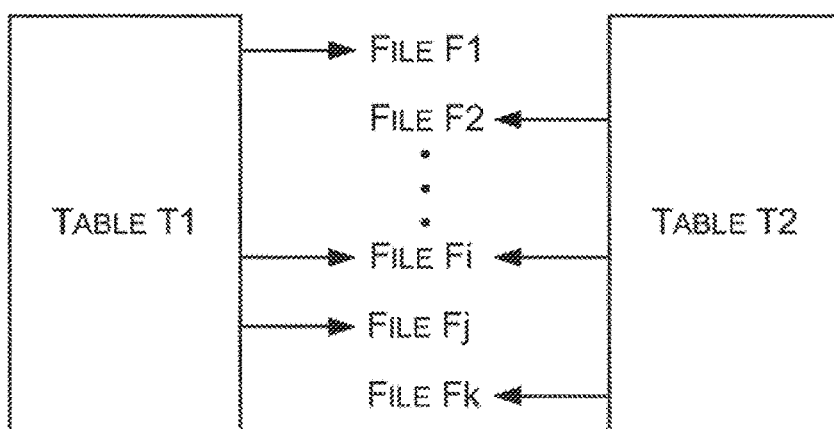

After cloned table T2 is created, new files can be added to either table T1 or T2 independently of the other table. Additionally, files can be deleted from either table T1 or T2 independently of the other table. For example, FIG. 10C shows the table and file associations after table T1 deleted file F2 and added new file Fj. Deleted file F2 is still visible to table T2, but new file Fj is not visible to table T2. In FIG. 10D, table T2 deleted file F1 and added new file Tk. File F1 remains visible to table T1, but new file Tk is not visible to table T1.

Although FIGS. 10A-10D illustrate the cloning of tables, alternate embodiments may clone catalog objects, schemas and databases in a similar manner. In particular embodiments, maps of all tables present in a schema are maintained as well as maps of all schemas present in a database. After cloning, the two schemas (or two databases) can be modified independently of one another.

The cloning systems and methods discussed herein improve the periodic loading of (and analysis of) new data or experimental data. Additionally, these systems and methods support quick updates of new data while requiring minimal additional computing or data storage resources.

Figure 11:
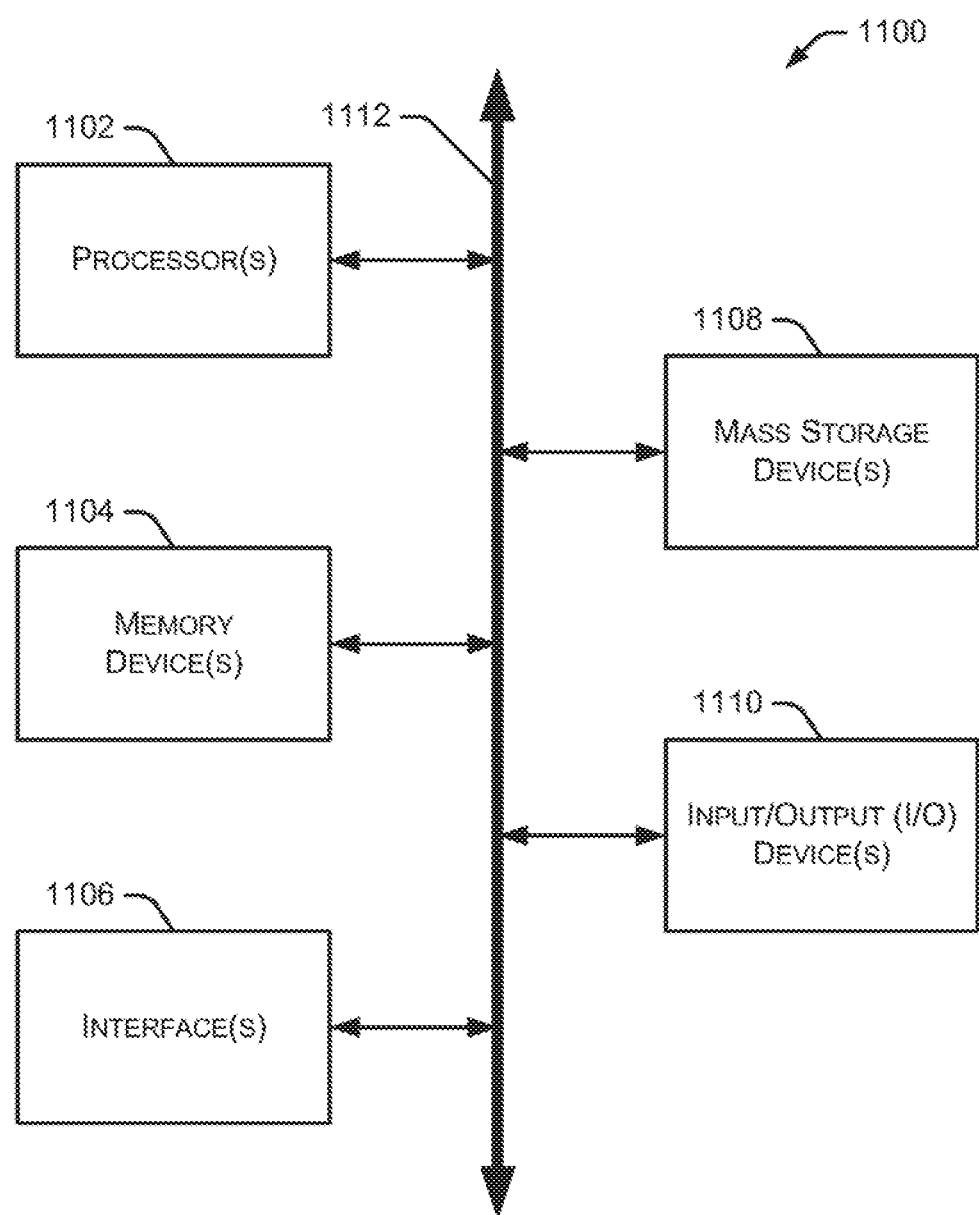
FIG. 11 is a block diagram depicting an example computing device.

FIG. 11 is a block diagram depicting an example computing device 1100. In some embodiments, computing device 1100 is used to implement one or more of the systems and components discussed herein. For example, computing device 1100 may allow a user or administrator to access resource manager 102. Further, computing device 1100 may interact with any of the systems and components described herein. Accordingly, computing device 1100 may be used to perform various procedures and tasks, such as those discussed herein. Computing device 1100 can function as a server, a client or any other computing entity. Computing device 1100 can be any of a wide variety of computing devices, such as a desktop computer, a notebook computer, a server computer, a handheld computer, a tablet, and the like.

Computing device 1100 includes one or more processor(s) 1102, one or more memory device(s) 1104, one or more interface(s) 1106, one or more mass storage device(s) 1108, and one or more Input/Output (I/O) device(s) 1110, all of which are coupled to a bus 1112. Processor(s) 1102 include one or more processors or controllers that execute instructions stored in memory device(s) 1104 and/or mass storage device(s) 1108. Processor(s) 1102 may also include various types of computer-readable media, such as cache memory.

Memory device(s) 1104 include various computer-readable media, such as volatile memory (e.g., random access memory (RAM)) and/or nonvolatile memory (e.g., read-only memory (ROM)). Memory device(s) 1104 may also include rewritable ROM, such as Flash memory.

Mass storage device(s) 1108 include various computer readable media, such as magnetic tapes, magnetic disks, optical disks, solid state memory (e.g., Flash memory), and so forth. Various drives may also be included in mass storage device(s) 1108 to enable reading from and/or writing to the various computer readable media. Mass storage device(s) 1108 include removable media and/or non-removable media.

I/O device(s) 1110 include various devices that allow data and/or other information to be input to or retrieved from computing device 1100. Example I/O device(s) 1110 include cursor control devices, keyboards, keypads, microphones, monitors or other display devices, speakers, printers, network interface cards, modems, lenses, CCDs or other image capture devices, and the like.

Interface(s) 1106 include various interfaces that allow computing device 1100 to interact with other systems, devices, or computing environments. Example interface(s) 1106 include any number of different network interfaces, such as interfaces to local area networks (LANs), wide area networks (WANs), wireless networks, and the Internet.

Bus 1112 allows processor(s) 1102, memory device(s) 1104, interface(s) 1106, mass storage device(s) 1108, and I/O device(s) 1110 to communicate with one another, as well as other devices or components coupled to bus 1112. Bus 1112 represents one or more of several types of bus structures, such as a system bus, PCI bus, IEEE 1394 bus, USB bus, and so forth.

For purposes of illustration, programs and other executable program components are shown herein as discrete blocks, although it is understood that such programs and components may reside at various times in different storage components of computing device 1100, and are executed by processor(s) 1102. Alternatively, the systems and procedures described herein can be implemented in hardware, or a combination of hardware, software, and/or firmware. For example, one or more application specific integrated circuits (ASICs) can be programmed to carry out one or more of the systems and procedures described herein.

Although the present disclosure is described in terms of certain preferred embodiments, other embodiments will be apparent to those of ordinary skill in the art, given the benefit of this disclosure, including embodiments that do not provide all of the benefits and features set forth herein, which are also within the scope of this disclosure. It is to be understood that other embodiments may be utilized, without departing from the scope of the present disclosure.

What is claimed is:

1. A system comprising:
   a memory to store an original schema associated with a set of data, wherein the original schema includes a plurality of objects; and
   one or more processors, operatively coupled to the memory, the one or more processors to:
      create a duplicate schema of the original schema by copying metadata associated with the plurality of objects without copying the set of data; and
      wherein to modify data associated with the original schema independently of the duplicate schema, the one or more processors further to:
         copy the plurality of objects associated with the original schema to a corresponding plurality of duplicate objects;
         modify the data in each of the plurality of duplicate objects; and
         update a metadata mapping between the plurality of duplicate objects and the original schema.

2. The system of claim 1, wherein the data is stored in files, and wherein the one or more processors are further to:
   execute data access requests directed to the data stored in the files by reading the duplicate schema of the original schema when the data is being recreated; and
   add additional files to either of the original schema or the duplicate schema of the original schema independently of another.

3. The system of claim 1, wherein to create the duplicate schema of the original schema the one or more processors are further to copy metadata associated with the data.

4. The system of claim 3, wherein to copy the metadata the one or more processors are further to copy an inventory of the data.

5. The system of claim 3, wherein to copy the metadata the one or more processors are further to copy information regarding the data that enables identification of the data without requiring access to the data.

6. The system of claim 1, wherein to identify the original schema in a database the one or more processors are to identify a logical grouping of data in the database.

7. The system of claim 1, wherein to modify the data associated with the original schema the one or more processors are to modify such that modified data is not visible to the duplicate schema of the original schema.

8. The system of claim 1, the one or more processors further to delete the duplicate schema of the original schema following completion of the modification of the data associated with the original schema.

9. A method comprising:
   creating a copy of an original schema without copying data associated with the original schema and by copying metadata of a plurality of objects associated with the original schema; and
   modifying, by one or more processors, data associated with the original schema independently of the duplicate schema of the original schema;
      wherein to modify the data associated with the original schema independently of the copy of the original schema, the one or more processors further to:
         copy the plurality of objects associated with the original schema to a corresponding plurality of duplicate objects;
         modify the data in each of the plurality of duplicate objects; and
         update a metadata mapping between the plurality of duplicate objects and the original schema.

10. The method of claim 9, wherein the data is stored in files, the method further comprising:
    executing data access requests directed to the data stored in the files by reading the duplicate schema of the original schema when the data is being recreated; and
    adding additional files to either of the original schema or the duplicate schema of the original schema independently of another.

11. The method of claim 9, wherein creating the duplicate schema of the original schema comprises copying metadata associated with the data.

12. The method of claim 11, wherein copying the metadata comprises copying an inventory of the data.

13. The method of claim 11, wherein copying the metadata comprises copying information regarding the data that enables identification of the data without requiring access to the data.

14. The method of claim 9, wherein identifying the original schema in a database comprises identifying a logical grouping of data in the database.

15. The method of claim 9, wherein modifying the data associated with the original schema comprises modifying such that modified data is not visible to the duplicate schema of the original schema.

16. The method of claim 9, the method further comprising deleting the duplicate schema of the original schema following completion of the modification of the data associated with the original schema.

17. A non-transitory computer-readable storage medium comprising instructions which, when executed by one or more processors, cause the one or more processors to:
    create a duplicate schema of an original schema, without copying data associated with the original schema, by copying metadata of a plurality of objects associated with the original schema; and
    modify data associated with the original schema independently of the duplicate schema of the original schema, wherein to modify the data, the one or more processors further to:
        copy the plurality of objects associated with the original schema to a corresponding plurality of duplicate objects;
        modify the data in each of the plurality of duplicate objects; and
        update a map of metadata between the plurality of duplicate objects and the original schema.

18. The non-transitory computer-readable storage medium of claim 17, wherein the data is stored in files, and wherein the one or more processors are further to:
    execute data access requests directed to the data stored in the files by reading the duplicate schema of the original schema when the data is being recreated; and
    add additional files to either of the original schema or the duplicate schema of the original schema independently of another.

19. The non-transitory computer-readable storage medium of claim 17, wherein to create the duplicate schema of the original schema the one or more processors are further to copy metadata associated with the data.

20. The non-transitory computer-readable storage medium of claim 19, wherein to copy the metadata the one or more processors are further to copy an inventory of the data.

21. The non-transitory computer-readable storage medium of claim 19, wherein to copy the metadata the one or more processors are further to copy information regarding the data that enables identification of the data without requiring access to the data.

22. The non-transitory computer-readable storage medium of claim 17, wherein to identify the original schema in a database the one or more processors are to identify a logical grouping of data in the database.

23. The non-transitory computer-readable storage medium of claim 17, wherein to modify the data associated with the original schema the one or more processors are to modify such that modified data is not visible to the duplicate schema of the original schema.

24. The non-transitory computer-readable storage medium of claim 17, the one or more processors further to delete the duplicate schema of the original schema following completion of the modification of the data associated with the original schema.

* * * * *

UNITED STATES PATENT AND TRADEMARK OFFICE
CERTIFICATE OF CORRECTION

| | | |
|---|---|---|
| PATENT NO. | : 11,151,160 B2 | |
| APPLICATION NO. | : 16/814443 | |
| DATED | : October 19, 2021 | |
| INVENTOR(S) | : Motivala et al. | |

It is certified that error appears in the above-identified patent and that said Letters Patent is hereby corrected as shown below:

On the Title Page

In item (56), page 2, Column 2, Line 12, please replace "Mazzafer et al." with --Mazzaferri et al.--

In item (56), page 2, Column 2, Line 43, please replace "Chen" with --Chen et al.--

Signed and Sealed this
Thirtieth Day of May, 2023

Katherine Kelly Vidal
*Director of the United States Patent and Trademark Office*